US006053034A

United States Patent [19]
Tsui et al.

[11] Patent Number: 6,053,034
[45] Date of Patent: Apr. 25, 2000

[54] METHOD FOR MEASURING FRACTURE TOUGHNESS OF THIN FILMS

[75] Inventors: Ting Y. Tsui, Palo Alto; Young-Chang Joo, Sunnyvale, both of Calif.

[73] Assignee: Advanced Micro Devices, Inc., Sunnyvale, Calif.

[21] Appl. No.: 09/168,570

[22] Filed: Oct. 9, 1998

[51] Int. Cl.⁷ ...................................................... G01N 3/48
[52] U.S. Cl. ................................................................ 73/81
[58] Field of Search ................................. 73/799, 81, 82, 73/150 R, 150 A

[56] References Cited

U.S. PATENT DOCUMENTS 5,324,694   6/1994   Petrak et al. .

OTHER PUBLICATIONS

Ahn, J. et al., "Hardness and Adhesion of Filmed Structures as Determined by the Scratch Technique," Adhesion Measurement of Thin Films, Thick Films, and Bulk Coatings, ASTM STP 640, pp. 134–157 (1978).

Oroshnik, J. et al., "Threshold Adhesion Failure: An Approach to Aluminum Thin–Film Adhesion Measurement Using the Stylus Method," Adhesion Measurement of Thin Films, Thick Films, and Bulk Coatings, ASTM STP 640, pp. 158–183 (1978).

Brown, H.R., "Mixed–Mode Effects on the Toughness of Polymer Interfaces," Journal of Materials Science, vol. 25, pp. 2791–2794 (1990).

Xiao, F. et al., "Phase Angle Effects on Fracture Toughness of Polymer Interfaces Reinforced with Block Copolymers," Macromolecules, vol. 27, No. 15, pp. 4382–4390 (1994).

Xu, G., et al., "Measurement of the Fracture Energy of $SiO_2$TiN Interfaces Using the Residually–Stressed Thin–Film Micro–Strip Test," Materials Research Society, vol. 458, pp. 465–470 (1997).

Smith, J.W., et al., "Measurement of the Fracture Toughness of Polymer–Non–Polymer Interfaces," Journal of Material Science, vol. 28, pp. 4234–4244 (1993).

Doerner, M.F., "Plastic Properties of Thin Films on Substrates as Measured by Submicron Identation Hardness and Substrate Curvature Techniques," Journal of Material Research, vol. 1, No. 6., pp. 845–851 (1986).

Larsen, T.A., "A Study of the Mechanics of Microidentation Using Finite Elements," Journal of Material Research, vol. 7, No. 3, pp. 618–626 (1992).

Oliver, W.C., "Measurement of Hardness at Indentation Depths as Low as 20 Nanometres," Microindentation Techniques in Materials Science and Engineering, ASTM STP 889, pp. 90–108 (1986).

(List continued on next page.)

*Primary Examiner*—Robert Raevis
*Attorney, Agent, or Firm*—Foley & Lardner

[57] ABSTRACT

A nanoindentation apparatus is used to measure the in-plane fracture toughness of a thin film formed on a substrate. One or more notches are formed in the thin film. An indenter is applied to the thin film near the notch or notches and a load is applied to the indenter to force it into the thin film. Because the substrate is softer than the thin film, the indenter does not penetrate the thin film, but "sinks in" to the soft substrate. The sink in effect enhances the tensile strain and stress at the notch. In one embodiment, both the penetration of the indenter into the thin film and substrate and the load on the indenter are measured. When the thin film fractures at the notch or notches, the indenter sharply sinks into the substrate. The thin film fracture toughness is then calculated based on the value of the load and penetration at the point of fracture using either finite element analysis or an analytical model. In a second embodiment, the cross-section of the notch or notches is measured after removing the indenter which has formed an indentation in the thin film. The indenter acts as a crack extension force. The thin film fracture toughness is then calculated based upon the geometry of a crack tip at the tip of the notch and using finite element analysis, or an analytical model, such as a Crack Tip Opening Displacement (CTOD) method.

34 Claims, 7 Drawing Sheets

OTHER PUBLICATIONS

Dugdale, D.S., "Wedge Indentation Experiments with Cold–Worked Metals," Journal of the Mechanics and Physics of Solids, vol. 2, pp. 14–26 (1953).

Dugdale, D.S., "Cone Indentation Experiments," Journal of the Mechanics and Physics of Solids, vol. 5, pp. 265–277 (1954).

Oliver, W.C. et al., "An Improved Technique for Determining Hardness and Elastic Modulus Using Load and Displacement Sensing Indentation Experiments," Journal of Material Research, vol. 7, No. 6, pp. 1564–1583 (Jun., 1992).

Wu, T.W. et al., "Micro–Indentation and Micro–Scratch Tests on Sub–Micron Carbon Films," Materials Research Society Symposium Proceedings, vol. 130, pp. 117–122 (1988).

Marshall, D.B. et al., "Measurement of Adherence of Residually Stressed Thin Films by Indentation," Journal of Applied Physics, vol. 56, No. 10, pp. 2632–2638 (Nov., 1984).

Tsui, T.Y. et al., "Nanoindentation and Nanoscratching of Hard Coating Materials for Magnetic Disks," Materials Research Society Symposium Proceedings, vol. 356, (1994).

Tsui, T.Y. et al., "Effects of Adhesion on the Measurement of Thin Film Mechanical Properties by Nanoindentation," Materials Research Society Symposium Proceedings, vol. 473, pp. 51–56 (1997).

Anderson, T.L., "Fracture Mechanics: Fundamentals and Applications, 2nd Ed.," CRC Press, Ch. 12, pp. 601–608; Ch. 3, pp. 117–122; Ch. 2, pp. 82–89; Ch. 12, pp. 610–626.

METHOD FOR MEASURING FRACTURE TOUGHNESS OF THIN FILMS

BACKGROUND OF THE INVENTION

This invention relates to methods for calculating the in-plane fracture toughness of a thin film formed on a substrate.

Thin films are very important in many applications. For example, thin films are used extensively in microelectronics applications where devices often have features of submicron size. Thin films are also used extensively in micromechanical applications for making devices such as microgears and accelerometers, and other applications such as for making hard disks in a hard drive and hard coating for gear boxes.

Determining the mechanical properties of thin films in these applications can be of critical importance. For example, a thin film having a large tensile stress may delaminate, causing device failure under certain conditions. The mechanical properties of a thin film material cannot simply be predicted based upon the properties of the bulk material for a number of reasons. First, the mechanical properties of the thin film generally differ from that material in its bulk form based on factors such as the particular technique for forming the film, and the conditions under which the film is formed. For example, a thin film formed on a substrate at high temperature and then cooled to room temperature may exhibit either a tensile or compressive stress due to the difference in the coefficient of thermal expansion between the film and the substrate.

Also, the underlying substrate in many applications will not have a surface that is smooth or of uniform composition. Instead, the substrate may have features with a varying topography due to thin film layers which are already formed and patterned. The mechanical properties of the thin film may vary across the surface of the film, depending upon both the thin film formation technique and the structure of the underlying substrate. Therefore, techniques for measuring the mechanical properties of thin films that can measure the properties of a small (often submicron) region are desired.

One technique for measuring certain mechanical properties of materials on a small scale uses load-displacement data from a load and displacement sensing system. An example of such a system is shown in FIG. 1. Typically, in such a system, an indenter with a small cross-section is applied to the surface of the material. This type of measurement technique is generally referred to as a microindentation or nanoindentation technique.

In a nanoindentation measurement, a load is applied to the indenter to force it into the material. As the indenter is forced into the material, the amount that the indenter is displaced into the material is measured. Concurrently with the measurement of the indenter displacement, the load applied to the indenter is measured. In general, for a relatively stiff material, the load increase will be greater for a given increase in indenter penetration (displacement) than for a less stiff material.

Because the indenter cross-section can be made quite small, a small area of a thin film may be probed. The mechanical properties of the thin film may therefore be mapped with submicron resolution. This is important for applications where the mechanical properties of the thin film may be expected to vary over a short distance across the surface of the film, such as when the underlying substrate has topological features of submicron size. The submicron resolution of nanoindentation techniques allows problem regions of the thin film to be identified, and potentially the problems in those regions may then be solved by adjusting the thin film deposition parameters, and/or the structure of the underlying substrate.

In a typical load and displacement measurement, the load on the indenter is increased to a maximum value, and then the load is decreased until the indenter is free from the material. Often at higher maximum loads, the material will remain deformed upon releasing the load on the indenter. A typical load/displacement behavior is shown in FIG. 2.

Using load-displacement data from a system similar to that of FIG. 1, Oliver and Pharr calculated the elastic modulus and hardness of bulk materials such as sapphire, quartz, tungsten, and aluminum, "An improved technique for determining hardness and elastic modulus using load and displacement sensing indentation experiments", J. Mater. Res., Vol. 7, No. 6, June 1992, pp. 1564–1583. However, unlike bulk materials, thin films have the added complication of an underlying substrate. When forcing an indenter into a thin film, not only will the thin film deform, but the substrate will deform as well. Therefore, calculation of the mechanical properties of a thin film involves taking into account the mechanical properties of the underlying substrate as well.

It is also known to measure certain mechanical properties of thin films using a nanoindentation technique. For example, Tsui et al. calculated the hardness of soft-film/hard-substrate systems such as Al/Glass, Al/ALON, and Al/sapphire in "Effects of Adhesion on the Measurement of Thin Film Mechanical Properties by Nanoindentation", Mat. Res. Soc. Symp. Proc. Vol. 473, March 31–April 3, 1997, pp. 51–56, while Doerner et al. investigated the strength of aluminum and tungsten films in "Plastic properties of thin films on substrates as measured by submicron indentation hardness and substrate curvature techniques", J. Mater. Res., Vol. 1, No. 6, November/December 1986, pp. 845–851 (1987). While there exist techniques for measuring certain mechanical properties of thin films, such as hardness and the elastic modulus, using a load and displacement sensing system, such techniques cannot be readily be applied to measure the in-plane fracture toughness of the thin film. Therefore, there exists a need for reliably and effectively measuring the in-plane fracture toughness, κ, of a thin film formed on a substrate using nanoindentation techniques.

SUMMARY OF THE INVENTION

An object of an embodiment of this invention is to provide a method for calculating the in-plane fracture toughness, κ, of a thin film on a substrate using an indenter of a load and displacement sensing system.

It is another object of an embodiment of this invention to provide a technique for calculating the in-plane fracture toughness of a thin film using an indentation "sink in" effect as a crack extension force where the substrate is softer than the thin film.

It is another object of an embodiment of this invention to provide a technique for calculating the in-plane fracture toughness of a thin film where the thin film is separated into strips and the in-plane fracture toughness of each strip is calculated.

It is another object of an embodiment of this invention to provide a technique for calculating the in-plane fracture toughness of a thin film where the thin film is formed of a single composition or of sublayers of the same or different compositions.

It is another object of an embodiment of this invention to provide a technique for calculating the in-plane fracture toughness, κ, of a thin film where the fracture toughness is calculated using finite element analysis, or an analytical model, such as a plane strain beam bending model.

In order to achieve these objects, an embodiment of the present invention provides a technique for measuring the in-plane fracture toughness, κ, of a thin film formed on a substrate. The present technique involves the formation of a thin film having at least one preformed notch. Advantageously, this measurement may be performed in-situ without destroying the entire thin film. The specific geometry of the at least one notch of the present invention is predetermined or may be measured, so that a model of the mechanical properties of the thin film including the notch can be readily determined. An indenter is applied to the thin film. A load is applied to the indenter, forcing it into the thin film, and thereby stretching the thin film. When the indenter reaches a displacement such that the stress on the thin film at the notch reaches a critical value, the thin film will crack and the indenter displacement will catastrophically (suddenly) increase as the indenter sinks sharply into the substrate. The in-plane fracture toughness, κ, can be calculated based upon the load-displacement data upon fracture of the thin film at the preformed notch.

The thin film may be provided with two notches formed in a long line, and an indenter is applied between and parallel to the notches. The indenter may be a Knoop or wedge shaped indenter. Alternatively, the indenter may be cylindrically shaped or of some other shape. The indenter is forced into the thin film with increasing load until the thin film fractures at the notches.

Alternatively in this embodiment, a thin film with a single notch formed in a closed loop is provided, and an indenter is applied near the center of the closed loop. The indenter may be any of cone, triangular, or square shaped, or of some other shape. The closed loop may be circular, triangular, square, or some other shape. The indenter is forced into the thin film with an increasing load until the thin film fractures at the notch.

The thin film is preferably formed of a harder material than the substrate. When the thin film is formed of a harder material than the substrate, and the indenter is forced into the thin film, the soft substrate yields to the indenter, causing a so-called "sink in" effect. The thin film is stretched due to the deformation of the soft substrate, thereby increasing the amount of tensile strain and stress at the notch for a given indenter load.

In another aspect of this invention, the thin film is separated into strips. The plane stress fracture toughness and the plane strain fracture toughness is determined by measuring the fracture toughness of strips with varying widths. The transition from the plane stress regime to the mixed regime and from the mixed regime to a plane strain regime is also determined based upon the fracture toughness of the strips with varying widths.

In another aspect of this invention, the thin film fracture toughness of a soft film riding "piggyback" on a harder thin film is determined. The piggyback structure benefits from the sink in effect because the substrate is softer than the intermediate thin film.

Another embodiment for calculating the in-plane fracture toughness, κ, of a thin film on a substrate is based on the size and geometry of the crack tip opening in the tip of a preformed notch in the thin film. In this embodiment, an indenter is forced into the thin film to make an indentation near the preformed notch. The indenter stretches the thin film, causing stress at the notch, which thereby widens the crack tip. The indenter is then removed. The size and geometry of the crack tip opening is determined after the indentation has been formed. The in-plane fracture toughness, K, of a thin film may then be calculated based on the size of the crack tip opening at a stress just before the point where the crack tip begins to further extend into the thin film. For example, the Crack Tip Opening Displacement (CTOD) method may be applied to measure the fracture toughness of the thin film. As one alternative, finite element analysis may be used instead of the CTOD method in calculating the in-plane fracture toughness. In this embodiment, a Knoop indenter, having a varying cross-section may be used, for example.

Further features will become more fully apparent in the following description of the embodiments of this invention and from the appended claims.

DETAILED DESCRIPTION OF THE PREFERRED EMBODIMENTS

Figure 1:
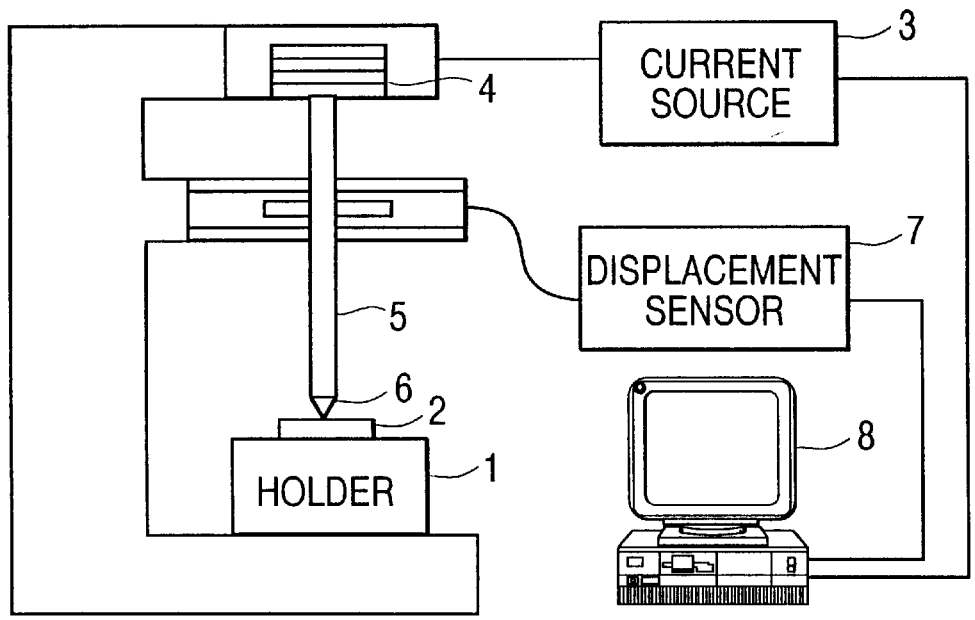
FIG. 1 is a schematic of a system for measuring the load and displacement of an indenter in a material.
Figure 2:
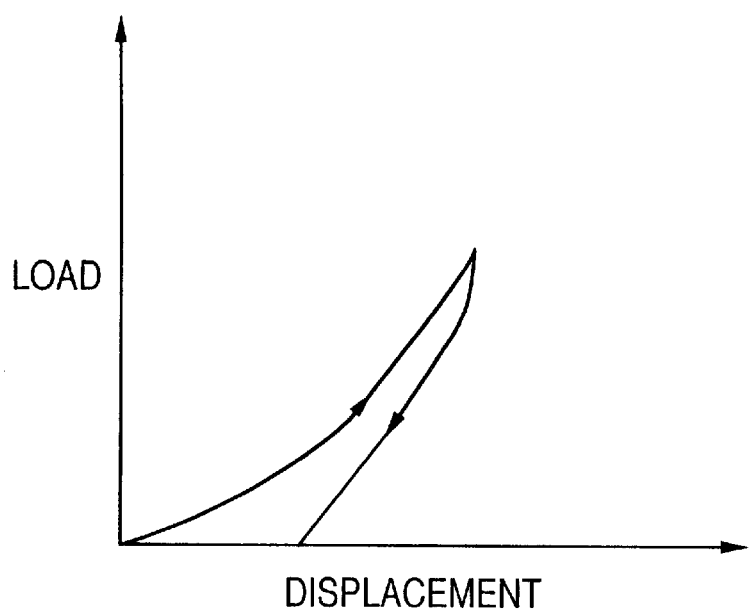
FIG. 2 illustrates a load-displacement curve for a load-displacement measurement.
Figure 3A:
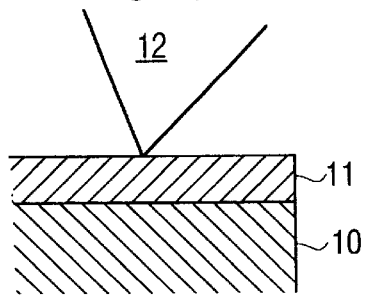
FIGS. 3A–3B show an indenter penetrating a thin film on a substrate with increasing load on the indenter for a conventional load-displacement measurement.
Figure 3B:
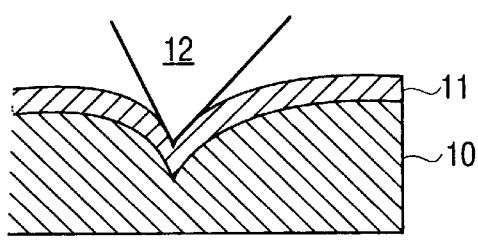

FIG. 1 shows a load and displacement sensing system employing an indenter which may be used for nanoindentation measurements. The present invention may include such a nanoindentation system, or other nanoindentation systems using an indenter known in the art. For example, such systems are sold under the trademark "Nanoindenter" by Nano Instruments of Knoxville, Tennessee. The load and displacement sensing system of FIG. 1 has a holder 1, upon which a sample 2 is placed. The sample 2 is a substrate upon which is a thin film (not shown). The system pushes an indenter 6 into the sample 2. It is preferred that at least the tip of the indenter 6 be made of a hard material, for example, diamond or SiC.

A current source 3 supplies a current to load application coils 4 which cause indentation column 5 to be displaced downward. The indenter 6 is attached on the bottom of the indentation column 5. When the current source 3 supplies current to the load application coils 4, the indentation column 5 pushes the indenter 6 downward towards and into the sample 2. The displacement of the indenter 6 is measured by means of a capacitive displacement sensor 7 that directly measures the displacement of the indentation column 5. A computer 8 receives the output from the displacement sensor 7 indicating the displacement of the indentation column 5 and indenter 6.

The computer 8 further controls the current source 3, setting the current source 3 to a desired current value to drive the load application coils 4. The load application coils 4 generate a load on the indentation column 5 that is transferred as the load on the indenter 6. The value of the load is determined by the amount of current provided to the coils 4 and increases with increasing current. The computer 8 monitors the current and the load, and may do so either continuously or in some other fashion, such as periodically, or only at the point when the thin film sharply sinks into the substrate.

Figure 4A:
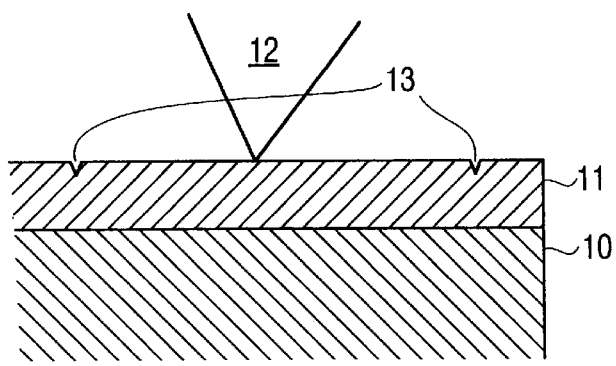
FIG. 4A is a side view of a first aspect of the first embodiment of the present invention employing two notches.
Figure 4B:
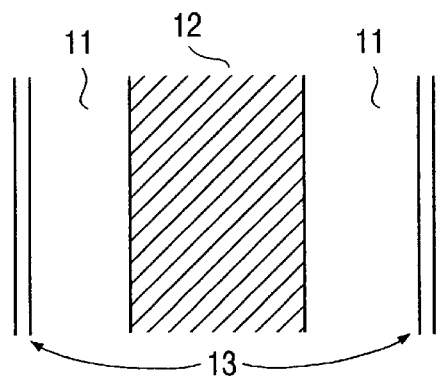
FIG. 4B is a top view of the aspect of the first embodiment shown in FIG. 4A.

FIG. 4A shows a first aspect of a first embodiment of the invention. In this aspect, the sample is a substrate 10 having a thin film 11 formed thereupon. The thin film 11 has two notches 13 formed upon the film at a predetermined location. In this specification, notch refers to an indentation, trench, or groove that may be of any size or shape that is either predetermined or can be measured before application of the indenter. One such example is shown in FIG. 4A as a V-shaped indentation. FIG. 4B is a top view of FIG. 4A and shows the notches 13 as long straight lines formed in the thin film 11. The notches 13 may be formed by any means that preferably provides well defined notches in the thin film 11. For example, the notches 13 may be formed by ion beam milling with a focused ion beam. Chemical etching methods such as plasma etching may also be used in forming the notches 13. Non-chemical methods of forming the notches 13, such as the scratch test method, may also be used.

The cross-section of the notch may then be measured. For example, the notches 13 may be cross-sectioned using focused ion beam milling. The cross-sectioned notches may then be imaged using an imaging device, such as a high resolution scanning electron microscope (SEM) or atomic force microscope (AFM). It is not necessary to measure the shape of the notch cross-section each time a notch is formed in the thin film. For example, if the substrate 10, thin film 11, and notch forming technique are the same in two separate measurements, it may be assumed that the notch cross-section will also be the same.

The substrate 10 may be composed of a single composition, or may include thin film layers on the substrate. The thin film 11 may be formed on the substrate 10 by conventional deposition methods such as sputtering, evaporation, and chemical vapor deposition. The thin film 11 may be formed of a single layer of material, or alternatively, of multiple sublayers of the same or different materials. For example, the thin film 11 may be made of a material such as Ti, while the substrate 10 may be Al. Alternatively, the thin film 11 may be formed of alternating sublayers of Ti and Al, while the substrate 10 is Al. Other examples of thin film-substrate systems include, but are not limited to silicon oxide-Al, W—Al, TiN—Al, and silicide-silicon.

Figure 4C:
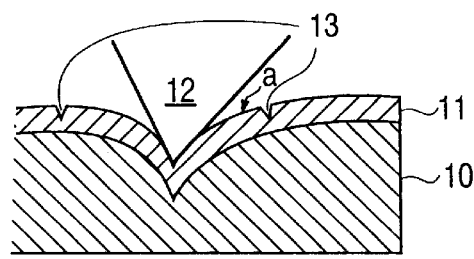
FIG. 4C is a side view of the aspect of the first embodiment of FIG. 4A upon penetration of the indenter into the thin film, though before the thin film fractures.
Figure 4D:
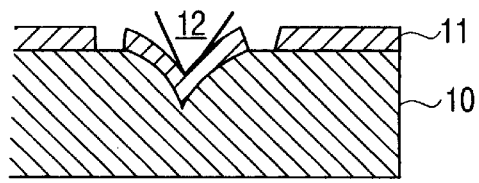
FIG. 4D is a side view of the aspect of the first embodiment of FIG. 4A after the thin film has fractured.

Preferably, the thin film 11 is formed of a harder material than the substrate 10. FIGS. 4C and 4D illustrates the displacement of the films when an indenter 12 is pushed into a thin film 11 when the underlying substrate 10 is softer than the thin film 11. Upon forcing the indenter 12 into the thin film 11, the substrate 10 tends to bend inwardly. This is known as the "sink in" effect. A tensile stress is created in the thin film 11 as the indenter 12 causes the thin film 11 to bend. The maximum tensile stress will occur at point a. The tensile stress is enhanced by the sink in effect because the deformation of soft substrate tends to increase the tensile strain on the thin film 11. As the indenter 12 continues to push into the thin film 11, the tensile stress will increase until the thin film 11 suddenly fractures as shown in FIG. 4D. FIG. 4D has been drawn to amplify the fracture of the film. In application, the fracture may not be as pronounced. The maximum tensile stress will occur at point a where the bending is maximum. The maximum tensile stress preferably occurs where the notches are formed. When the thin film 11 fractures, the indenter will no longer be restrained by the thin film 11, and the indenter 12 will suddenly push the fractured thin film 11 into the softer underlying substrate 10 at a much greater rate.

Figure 5:
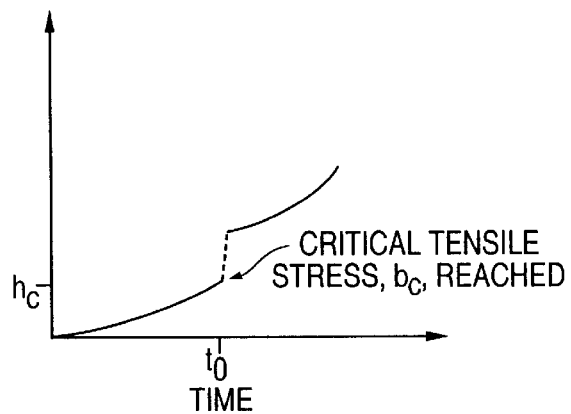
FIG. 5 shows the displacement as a function of time for the first embodiment of the present invention.

FIG. 5 illustrates the displacement of the indenter 12 as the load on the indenter 12 is increased. Initially, as the load on the indenter 12 is increased, the penetration or displacement continuously and smoothly increases. However, at the critical tensile stress, $b_c$, where the thin film 11 fractures, the rate of indenter penetration sharply increases as the indenter 12 pushes the fractured thin film into the soft substrate. As the load is increased after fracture, the indenter penetration is again generally continuous.

In a preferred embodiment, the load on the indenter 12 is increased at a constant rate. However, the invention does not require that the load be increased at a constant rate, and instead may be increased at varying rates. Other displacement techniques are contemplated, such as increasing the load to a point, holding it constant for a period of time, and then increasing it again. As the indenter 12 is pushed into the thin film 11 and substrate 10, both the displacement and the load are measured. Preferably, the computer 8 will monitor the load and displacement of the indenter 12 continuously. However, the computer 8 will at least monitor the load and displacement at the time when the thin film 11 fractures, i.e., the computer 8 will at least monitor the critical load, $P_C$, and the critical displacement, $h_C$.

In this aspect of the first embodiment, the indenter may be a Knoop, wedge, or cylindrical indenter, or an indenter with another cross-section shape. FIG. 4B shows a wedge indenter. The long axis of the wedge indenter is oriented parallel to the line notches in the thin film. The wedge indenter is preferably applied at a point near the center between the two notches 13. The wedge indenter may also be applied to a point other than the center between the notches 13. However, in the instance that the indenter 12 is applied at a point other than the center between the notches 13, the fracture in the thin film 11 will likely occur first at the notch closest to the indenter. Upon fracture of the thin film 11 when critical tensile stress, $b_c$, is reached, the value of the critical load, $P_C$, on the indenter 12, and value of the indenter critical displacement or penetration, $h_C$, is noted by the computer 8.

Preferably, the computer 8 is configured to automatically measure the displacement and load precisely at the time when the, thin film fractures and the indenter penetration rate sharply increases. The occurrence of the fracture may be triggered in the computer by monitoring the rate of displacement of the indenter. When this rate of increase is beyond a set threshold level, the computer flags the time, displacement, and load.

Because the substrate 10 is softer than the thin film 11, the tensile stress as a function of indenter displacement may now be calculated using a simple analytical model. For example, the thin film deflection may be modeled using the plane-strain beam bending model, the single edge notched bend model, or some other model appropriate to the loading conditions and the geometry of the thin film and notch. The calculation of the fracture toughness at a notch for several models is known for bulk materials and outlined in literature on the mechanical properties of materials. For example, such solutions of the fracture toughness for bulk materials are given in *Fracture Mechanics,* T. L. Anderson, Second edition, CRC Press, pp. 601–608, which is herein incorporated by reference. We have discovered that such models may be applied to thin films and are useful for modeling the fracturing of the thin film when an indenter is used. The values of the fracture toughness may be calculated using a computer.

Figure 9:
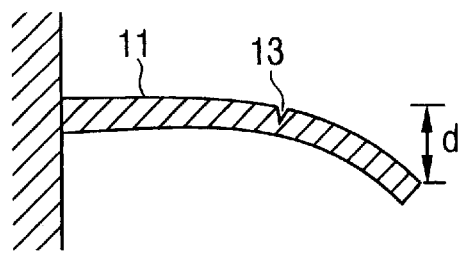
FIG. 9 is an illustration of the plane-strain beam bending model.

FIG. 9 illustrates the plane-strain beam bending model. The left side of the film is considered fixed, while the right side of the film is deflected downward a distance d. In this case, the distance d represents the critical displacement, $h_C$, where the thin film fractures, as discussed above. The tensile stress at the notch will be a function of the film deflection, and the critical load applied, $P_C$.

Alternatively, the thin film fracture toughness, κ, may be calculated from the geometry of the notch using finite element analysis. Finite element analysis techniques are well known in the art. See for example, Lausen et al., "A study of the mechanics of microindentation using finite elements", J. Mater. Res., Vol. 7, No. 3, March 1992, pp. 618–626, which is herein incorporated by reference. The finite element analysis may be performed using a computer with software such as ANSYS, which is sold by ANSYS, Inc.

Preferably, the thin film fracture toughness calculation, whether based on an analytical model or finite element analysis, is performed by a computer as the load and displacement data is gathered by the computer. Therefore, the fracture toughness, κ, measurement may be done in-situ in real time. The thin film calculation may be performed using the computer which controls the indenter and monitors the load and displacement data, or by a separate computer.

This method of determining the thin film fracture toughness allows for in-situ testing of thin films in a device fabrication line. For example, this method may be implemented in a semiconductor device fabrication line. The notches may be formed on the thin film on a partially completed device at any stage of forming the device. The thin film may then be tested, and if the thin film fracture toughness does not meet required specifications, the device is tagged as defective, and further expensive processing is not wasted on the defective device.

Figure 6:
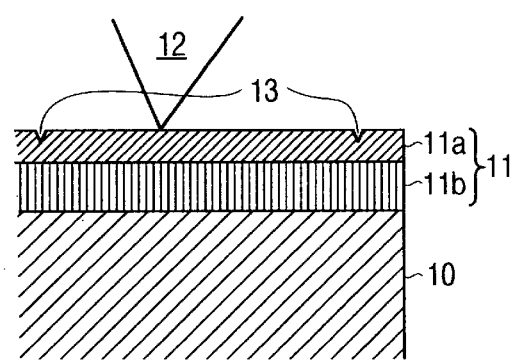
FIG. 6 is a side view of another aspect of the first embodiment of the present invention.

FIG. 6 shows a side view of another aspect of the first embodiment. In this aspect, the thin film 11 is formed of sublayers 11a and 11b. Sublayer 11b is formed on the substrate 10, and is of a harder material than the substrate 10. Sublayer 11a is formed on sublayer 11b and may be either harder, softer, or of the same hardness as sublayer 11b. Preferably, sublayer 11a is thinner than sublayer 11b. In this aspect of the first embodiment, even when sublayer 11a is of a material softer than the substrate, the measurement benefits from the "sink in" effect of the substrate because of the hard sublayer 11b that is between the substrate and the sublayer 11a. The stress on the sublayer 11a will be enhanced due to this sink in effect. This aspect of the first embodiment may be referred to as a "piggyback" configuration because the top sublayer 11a, whose in-plane fracture is of interest in this aspect, rides "piggyback" on the sublayer 11b.

In this aspect of the first embodiment, a notch is formed in the top sublayer 11a because the fracture toughness of the top sublayer is of interest. As with the first aspect of the first embodiment, the indenter is pressed into the thin film until fracture occurs, and the load-and displacement of the indenter are monitored by the computer 8. However, in this aspect, only the top sublayer 11a having the notch fractures.

The in-plane fracture toughness of the top sublayer 11a is calculated in a manner similar to the first aspect of the invention, i.e., using either an analytical model, such as the plane-strain beam bending model for the top sublayer 11a or by using finite element analysis. Although this "piggyback" aspect is especially advantageous for measuring the fracture toughness of soft thin films, the fracture toughness of harder thin films may also be determined.

Figure 7A:
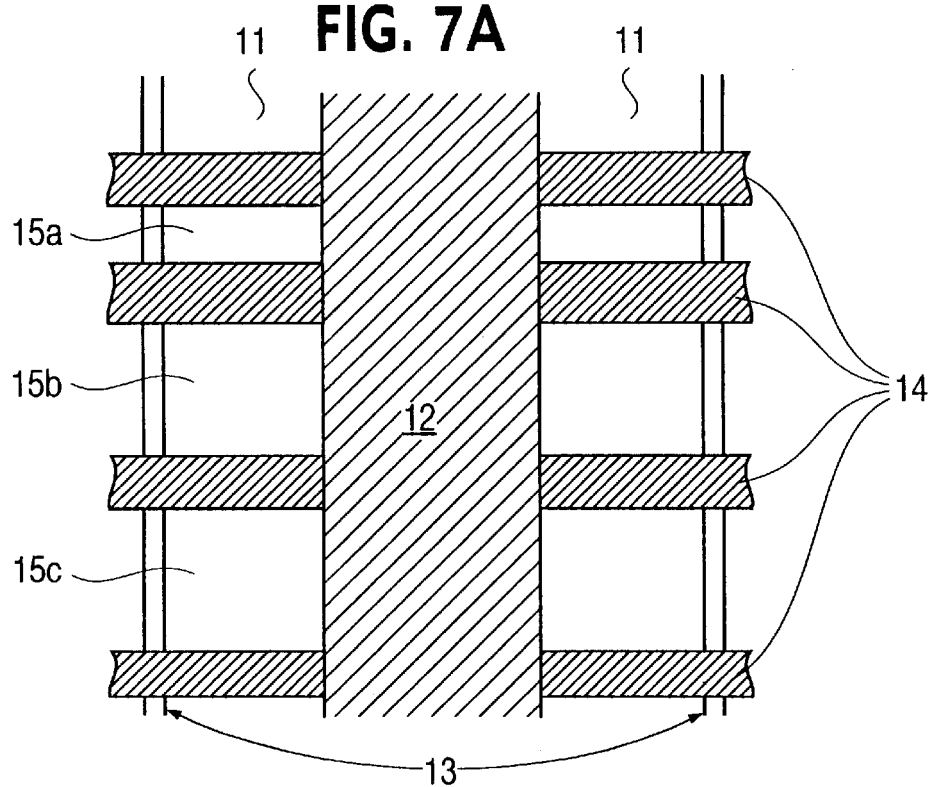
FIG. 7A is a top view of another aspect of the first embodiment of the present invention.

FIG. 7A shows a top view of another aspect of the first embodiment. This aspect of the first embodiment is similar to the aspect of the first embodiment in FIG. 4A, but in this aspect the thin film is separated into a number of strips 15a, 15b, 15c, etc. Slots 14 are formed in the thin film to form the strips. The slots may be formed by techniques similar to those for forming the notches, i.e. ion beam milling or chemical etching. The slots are formed all the way to the underlying substrate 10 to ensure that the strips are separated. The strips may have the same width or varying widths.

In this aspect of the first embodiment, the notches 13 are formed so that they intersect the slots 14. FIG. 7A shows the slots intersecting the trenches at a right angle. However, the slots may intersect the trenches at an angle other than a right angle.

The indenter 12, which may be a Knoop, wedge, cylindrical, or other indenter is applied to the thin film across one of the strips and between the notches. FIG. 7A shows the indenter at a right angle to the strips. However, the indenter may intersect the strips at an angle other than a right angle, as long as the indenter crosses at least one of the strips.

If the strips are of different widths, it is preferable that the indenter be applied across only one of the strips at a time. If the indenter is applied across several strips of different widths, when one of the strips fractures, the indenter will not sink as sharply into the substrate because the remaining unfractured strips will restrain the indenter. However, if the indenter is across only one strip, then upon fracture of the strip, the indenter will sharply sink into the substrate. If all the strips are the same width, then the strips should fracture simultaneously and it makes little difference if the indenter is across one or several strips.

In the case that several strips of different widths are formed, it is preferred that the fracture toughness of the individual strips be determined using separate indenters, or the same indenter at different times. The width of the slots may be chosen to more easily apply an indenter to just one strip. If separate indenters are used, they may be applied either simultaneously, or at different times to the individual strips.

Figure 7B:
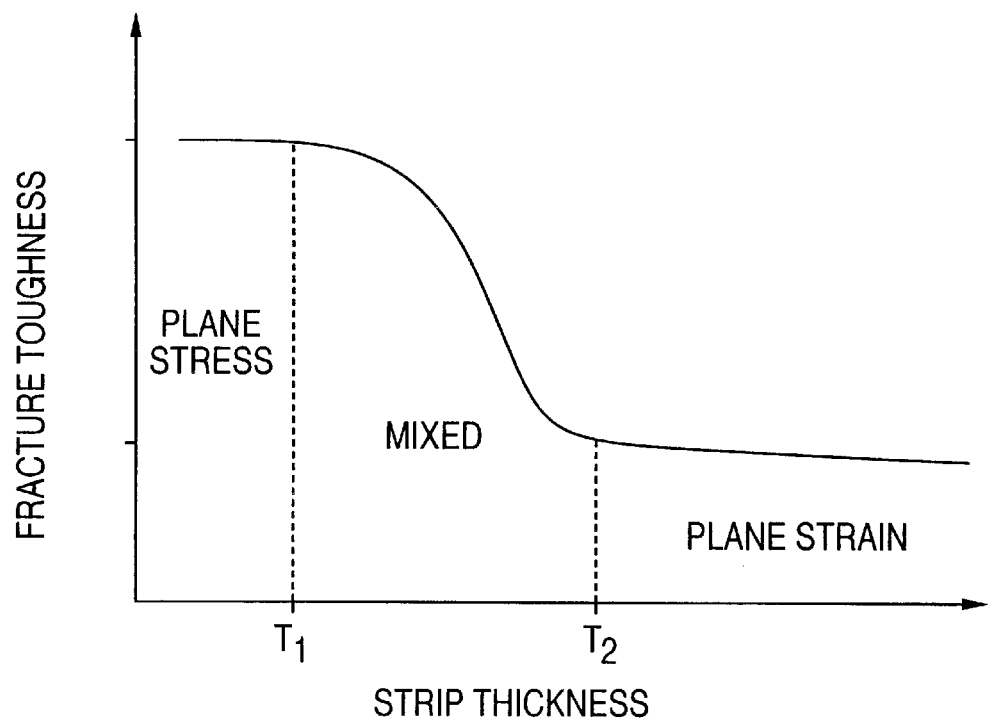
FIG. 7B shows the behavior of the thin film fracture toughness as the strip width of the thin film increases.

The load on the indenter is increased until the thin film strips fracture at the notch. The load and displacement at which the thin film strips fracture will depend upon the width of the thin film. FIG. 7B shows the typical behavior of the fracture toughness as the width of the strip is increased. The fracture toughness of the strips will be become stable above a certain strip width, i.e., as the strip width increases beyond a certain strip width, the fracture toughness will become constant. The value of the fracture toughness for these relatively wider strips is called the plane strain fracture toughness value. The fracture toughness of very narrow strips should also be constant and is called the plane stress fracture toughness. As the width of the strip is increased from the very narrow regime, the fracture toughness will change and will be in the mixed regime between the plane stress fracture toughness and the plain strain fracture toughness. $T_1$, the transition width from the plain stress regime to the mixed regime is shown in FIG. 7B. $T_2$, the transition width from the mixed regime to the plane strain regime is also shown in FIG. 7B.

In this aspect of the first embodiment, the transition widths, $T_1$ and $T_2$, are determined by measuring the fracture toughness of varying widths of strips of the thin film. The strip width where the fracture toughness first begins to change is the transition width, $T_1$, while the strip width where the fracture toughness becomes constant again is the transition width, $T_2$. The plain stress fracture toughness, which is the fracture toughness of the very narrow strips is also determined, as well as the plain strain fracture toughness which corresponds to the very wide strips.

Figure 8A:
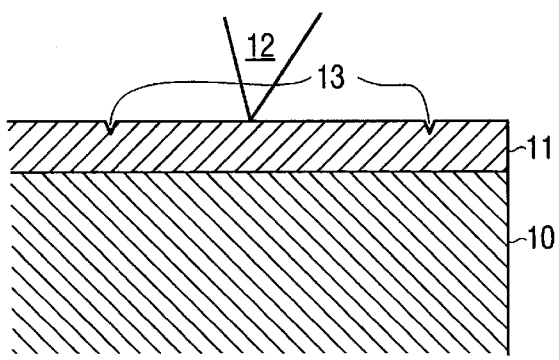
FIG. 8A is a side view of a further aspect of the first embodiment of the present invention employing a single notch.
Figure 8B:
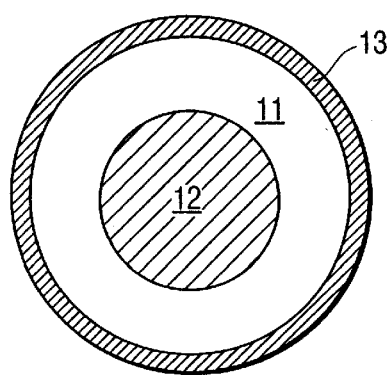
FIG. 8B is a top view of the aspect of the first embodiment shown in FIG. 8A.

FIG. 8A shows a side view of another aspect of the first embodiment. This aspect of the first embodiment is similar to the aspect of the first embodiment in FIG. 4A, with the exception that a single notch 13 is formed in a closed loop in the thin film 11, instead of two parallel line notches. In FIG. 8A the closed loop is a circle, but other shapes such as a triangle, or square may also be used. FIG. 8B shows a circular notch 13 formed in the substrate. In this aspect of the first embodiment, the indenter 12 has a shape which allows it to fit entirely within the closed loop. For example, the indenter may be conical, square or triangular shaped, or have some other shape. In FIG. 8B, the indenter has a conical shape. The conical indenter is applied near the center of the circle defined by the notch 13.

The load on the conical indenter is increased until the thin film 11 fractures at the location of the notch. Upon fracture of the thin film 11 when critical tensile stress, bc, is reached, the value of the load on the indenter 12, and value of the indenter displacement or penetration is noted by the computer 8.

In this aspect of the first embodiment, a variation of the plane-strain beam bending model must be used because this aspect of the invention has a single circular notch instead of the two line notches of the previous aspects of the first embodiment. The relationship between the tensile stress at the notch 13 and the cone indenter penetration may be determined using any of numerous known analytical models or, alternatively, finite element analysis may be used. The thin film fracture toughness, κ, may then be calculated based on the stress at the notch upon fracture.

As can be seen from the examples given, any number of notches of various geometries may be used, as long as an analytical model or finite element analysis (or other known calculation techniques) are available to calculate the necessary factors for determining the fracture toughness.

In a second embodiment of the invention, the in-plane fracture toughness may be calculated without using load and displacement data. Therefore, in the second embodiment, an indenter system which does not monitor the load and displacement of the indenter may be used. In this embodiment, the in-plane fracture toughness may be calculated simply by inspecting the notch depth and shape after the indentation process. For films where crack tip blunting occurs, such as with ductile metal films, the fracture toughness can be determined from the crack shape after the indentation and an analytical model which relates the crack shape to the fracture toughness. An example of an analytical model relating the crack shape to the fracture toughness is the crack tip opening displacement method (CTOD). According to the CTOD method, the fracture toughness, κ, may be expressed as:

$$\kappa = \sqrt{mE\delta\sigma}. \quad [1]$$

In the above equation, E and σ are the elastic modulus and the yield strength of the thin film material, respectively, δ is the amount of the crack tip opening just before crack tip extension into the thin film, and m is a dimensionless constant that is approximately 2.0 for the plane strain condition. FIG. 10B shows the amount of the crack tip opening, δ.

Another example of an analytical model relating the crack shape to the fracture toughness is the strip yield model. The strip yield model is similar to the CTOD method, but assumes plain stress conditions where m is approximately 1.0.

The number of preformed notches in this embodiment may be one or more. The preformed notches are formed in a similar fashion to the first embodiment, i.e., by ion beam milling, chemical etching, a scratch test method, or other methods known to preferably provide a well defined notch. For example, as with other embodiments, the notches may be cross-sectioned using a focused ion beam milling technique and then imaged using an imaging device such as a high resolution SEM or AFM.

After the notch is formed in the thin film, an indenter is applied to the thin film on the substrate, just as with the first embodiment. The thin film is preferably of a harder material than the substrate in order to take advantage of the "sink in" effect, as with the first embodiment. As with the first embodiment, the thin film may be a single layer, or multiple layers, and the substrate may include thin film layers. In this second embodiment, the thin film may also be in a "piggyback" configuration, with the film of interest being the top sublayer of the thin film. In this embodiment, the thin film is a material in which crack tip blunting occurs so that the CTOD method or a similar method may be applied.

At least one notch should be formed in the thin film in this embodiment. For example, if a single line notch is formed in the thin film, a Knoop, wedge, or cylindrical indenter may be applied to the thin film. The long axis of the indenter should be applied parallel to the notch. However, in this embodiment, it is not necessary that the load on the indenter or penetration depth of the indenter be monitored while the indenter is penetrating the thin film.

As an alternative, the notch may be a closed loop which may be circular, square, triangular, or some other shape. In this specification, the term closed loop includes loops which are nearly, but not completely closed.

As the indenter penetrates the thin film, a tensile stress is created in the thin film at the location of the notch. The tensile stress tends to widen, and if large enough, will deepen the notch. In this embodiment, the indenter penetrates the thin film to widen the notch, but the indenter need not penetrate the thin film to beyond the point where catastrophic crack growth occurs.

Figure 10A:
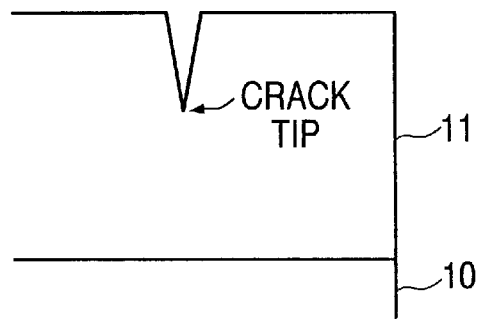
FIGS. 10A–10C show the widening and then extension of a crack tip of a second embodiment of the present invention.
Figure 10B:
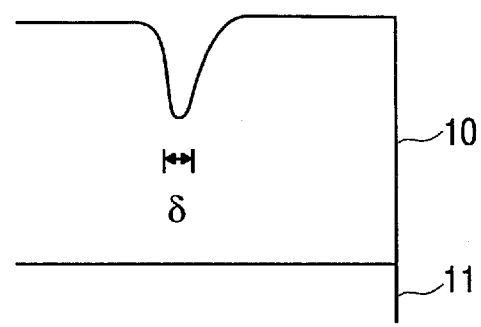
Figure 10C:
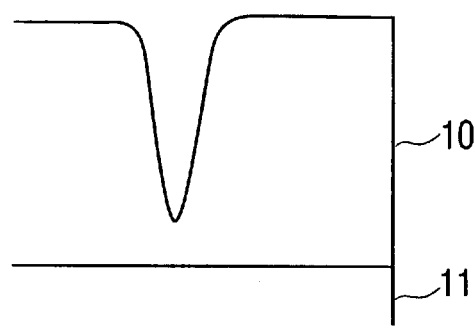

FIGS. 10A and 10B show a notch before and after applying the indenter, respectively. In FIG. 10B the crack tip has widened, but has not further extended into the thin film. FIG. 10C shows the notch when sufficient stress has been applied to cause the crack tip to further extend, i.e., beyond the initial extension of the preformed notch before application of the indenter into the thin film. As shown in FIG. 10B, δ is the size of the crack tip opening of the notch just before the crack tip begins to further extend into the thin film. FIGS. 10A and 10B demonstrate that the crack tip opening will grow substantially upon applying the indenter to the thin film. The thin film fracture toughness, κ, may then be calculated using an analytical model such as equation 1 based upon the CTOD method. The values for E, the elastic modulus, and σ, the yield strength, of the thin film may be found in reference books listing the mechanical properties of the thin film material. Preferably, however, the values for E, the elastic modulus, and σ, the yield strength, of the thin film material are predetermined using a measurement device such as a nanoindentation system.

Alternatively, the thin film fracture toughness may be calculated using known finite element analysis. Preferably, the finite element analysis calculation is performed on a computer.

Figure 11:
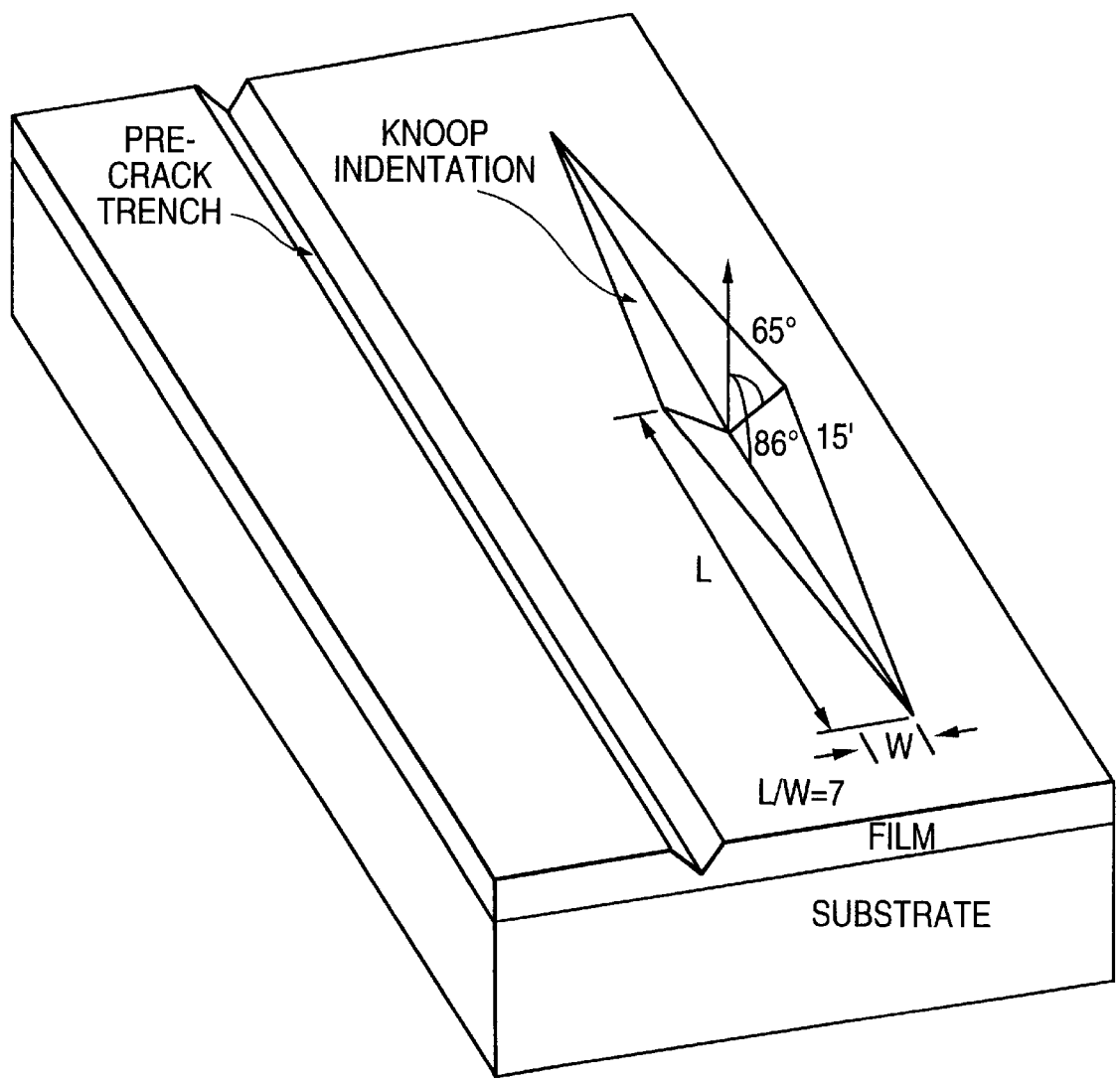
FIG. 11 shows the shape of a Knoop indentation and the preformed notch in the thin film for the second embodiment of the present invention.

A fracture toughness measurement was performed using a thin film composed of six titanium/aluminum bilayers sputtered on an aluminum alloy disk. The thickness of the aluminum and titanium layers are ~200 nm and ~700 nm, respectively. A preformed notch was formed in the thin film using focused ion beam milling. A 30 KV Gallium ion beam with a current at 1000 nA was used to manufacture a 200 μm long, ~1 μm wide and ~3 μm deep preformed notch. The cross section of the preformed notch was determined using a scanning electron micrograph prior to the fracture measurement. The tip of the notch extended into the fourth titanium layer from the top. A Knoop indenter was applied to the thin film approximately 20 μm from and parallel to the preformed notch. The Knoop indenter was a sharp diamond indenter. FIG. 11 shows the shape of a Knoop indentation and the preformed notch in the thin film. A load was applied to the indenter to force it into the thin film. For a softer substrate, as the load is applied, the thin film sinks into the softer substrate. The thin film is stretched and a tensile stress is generated at the notch. The amount of stress generated at a particular location of the notch will depend upon the amount the thin film is stretched at that location. The portions of the Knoop indenter that have the greatest cross-section (usually near the middle) will tend to generate the greatest tensile stress in adjacent portions of the notch, because those portions of the Knoop indenter will produce the greatest amount of stretching of the thin film. Therefore, the tensile stress at the notch will be greatest in those portions near the center of the Knoop indenter, and will be less in those portions away from the center of the Knoop indenter.

After a load was applied to the indenter, the indenter was removed from the thin film, and several portions of the notch were cross-sectioned by focused ion beam milling to inspect the amount of crack tip blunting and crack growth at various locations. The cross-sections of the notch after the indenter had been applied was determined using a scanning electron micrograph. The crack had extended in the portions of the notch near the center of the Knoop indentation, while portions further away from the center showed crack tip widening, but no crack extension. The value for the amount of crack tip opening, δ, in the CTOD method was assumed to be the value of the crack tip opening of the portion of the notch which exhibited the widest crack tip, but showed no crack tip extension. This value, δ, was found to be ~60 nm. From previous measurements, the value of the titanium thin film yield strength, σ, was found to be ~330 MPa, while the elastic modulus, E, was 120 GPa. Therefore with m=2, and using equation 1 the fracture toughness of the titanium layer is ~1.80 MPa√m.

In this example of the second embodiment, a Knoop indenter with varying cross-section was used to provide a varying stress along a line notch. Alternatively, the notch may be a closed loop, such as a circle, and an indenter, such as a square indenter, may be used to provide a varying stress along the closed loop notch.

In addition to the thin film fracture toughness, other mechanical parameters of the thin film may be calculated using an indenter. For instance, in the above example, with multiple alternating sublayers of titanium and aluminum on an aluminum substrate, the fracture mode of mixity at the crack tip may be determined using finite element analysis. The mode of mixity is the amount of mode I stress, $\kappa_I$, and mode II stress, $\kappa_{II}$. In general, the mode of mixity will change with increasing indenter depth. For the titanium and aluminum system mentioned above, finite element analysis showed that influence of the mode II shear deformation increased with indenter depth.

Figure 12:
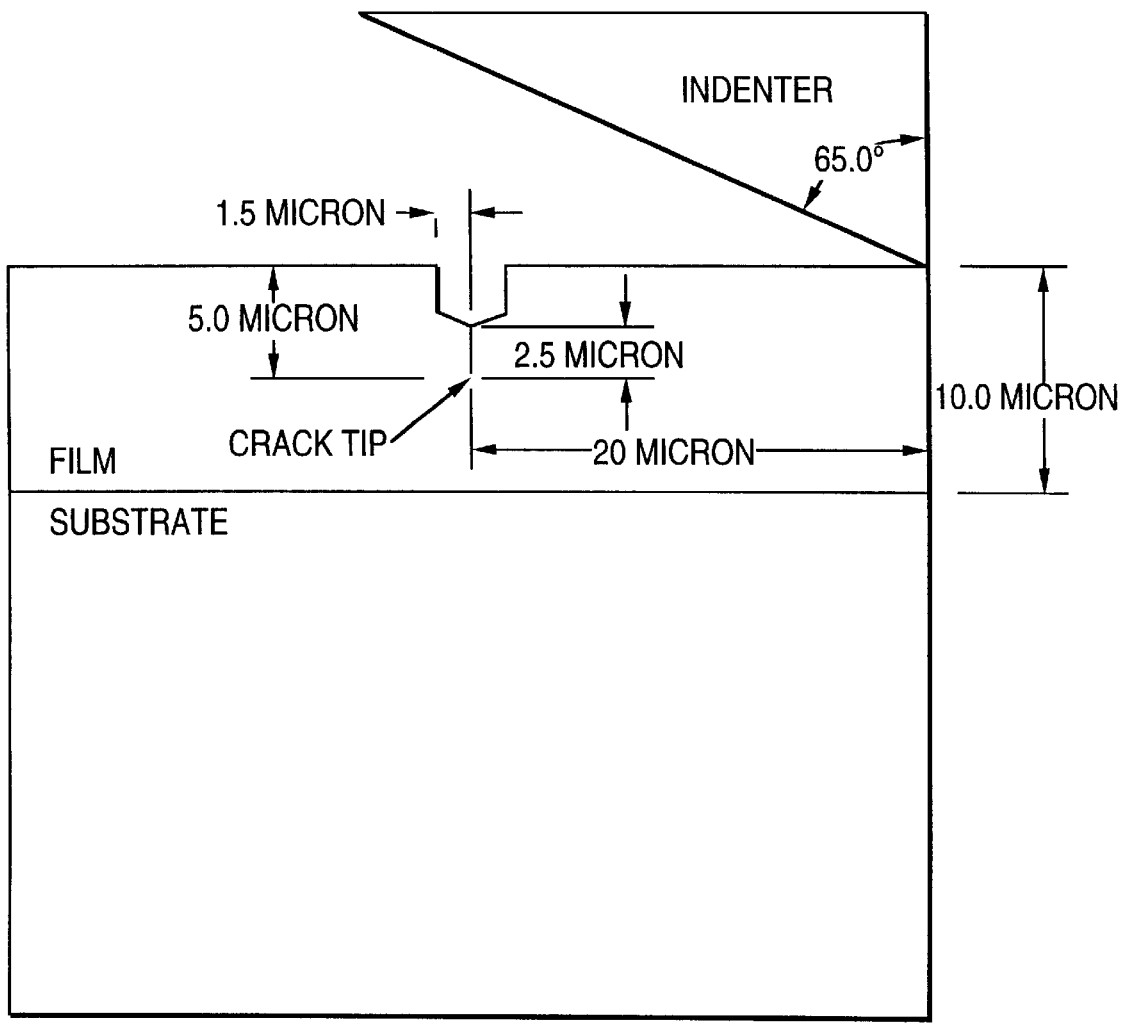
FIG. 12 shows the notch geometry for an embodiment of the invention.

In another aspect of this invention the mode of deformation near the crack tip was investigated with finite element analysis simulation using ANSYS software. Plain strain elements with eight nodes (Plane 82) and contact elements (Contact 48) were used. A model with a 10 μm thick monolithic silicon oxide film on an aluminum substrate was simulated. The crack tip geometry is shown in FIG. 12. The contacting interface between the indenter and the film was modeled with static friction coefficient (u) equals to 1. The normal and sticking contact stiffness values are 700 MN/m and 7 MN/m, respectively. These values are chosen such that excessive contact element overlapping can be avoided during the simulations. Dynamic friction is set at the same value as the static friction coefficient. During the simulation, the thin film is assumed to adhere perfectly to the aluminum substrate. The indenter is modeled as a wedge with an apex angle 130° and a flat tip 1 μm across. The model consists of 4383 elements and 7529 nodes. The silicon oxide film being modeled was assumed to have an elastic modulus of 80 Gpa and a Poisson's ratio of 0.20. The film is assumed to deform elastically. The aluminum substrate elastic modulus and Poisson ratio are 70 Gpa and 0.34, respectively. The 0.4% yield strength of the aluminum is assumed to be 280 MPa. All of the elastic and plastic properties of the modeling materials are assumed to be isotropic. Both of the film and the substrate modeled are assumed to be void free. Penalty method, Newton-Raphson method, elastic columbic friction option, and large deflection option were utilized in the finite element computations.

Other aspects of the invention are also envisioned. For example, although it is preferred that the first aspect of the first embodiment have two line notches, a single line notch may instead be formed. Also, the underlying substrate may be as hard or harder than the thin film as long as the notched thin film will fracture upon applying a sufficient load on the indenter, and as long as the time at which the fracture occurs may be determined.

Although the invention has been described and illustrated, it should be understood that the description is for illustration and example only, and is not meant to limit the spirit and scope of this invention.

What is claimed is:

1. A method for determining the in-plane fracture toughness of a thin film on a substrate using an indenter, comprising:
applying the indenter to the thin film to form an indentation, where the thin film has at least one preformed notch;
calculating the in-plane fracture toughness of the thin film.

2. The method as recited in claim 1, further comprising:
separating the thin film into strips, each strip having a width;
where the step of calculating the in-plane fracture toughness step comprises calculating the in-plane fracture toughness of each strip.

3. The method as recited in claim 2, further comprising:
calculating the thin film plane strain fracture toughness and the plane stress fracture toughness based on the in-plane fracture toughness of the strips.

4. The method as recited in claim 2, further comprising:
calculating a first strip transition width, $T_1$, and a second strip transition width, $T_2$, based upon the in-plane fracture toughness of the strips, where $T_1$ is the transition width between a plain stress fracture toughness regime and a mixed regime, and $T_2$ is a transition width between a mixed regime and a plain strain fracture toughness regime.

5. The method as recited in claim 1, where the at least one preformed notch is formed by one of scratch test method, ion beam milling, and chemical etching.

6. The method as recited in claim 1, where the at least one preformed notch is formed by ion beam milling using a focused ion beam.

7. The method as recited in claim 1, further comprising:
measuring a cross-section of the at least one preformed notch by one of an atomic force microscope and a scanning electron microscope.

8. The method as recited in claim 1, where the at least one preformed notch comprises two notches positioned apart at a spaced distance, and the indenter is applied between the two notches.

9. The method as recited in claim 1, where the indenter is one of a Knoop indenter, a wedge indenter, and a cylindrical indenter.

10. The method as recited in claim 1, where the thin film is of a first material and the substrate is of a second material different from the first material.

11. The method as recited in claim 10, where the first material is harder than the second material, and a sink-in effect enhances the tensile strain on the thin film.

12. The method as recited in claim 10, where the thin film fracture toughness is calculated using values of elastic constants of the first material and of the second material.

13. The method as recited in claim 1, where the at least one preformed notch is a line notch and the fracture toughness is calculated using one of an analytical model and finite element analysis.

14. The method as recited in claim 13, wherein the fracture toughness is calculated using one of a plane strain beam bending model, and a single edge notched bend model.

15. The method as recited in claim 1, where the at least one preformed notch is a single notch formed as a closed loop in the thin film.

16. The method as recited in claim 15, where the closed loop is one of a circle, a triangle, and a square, and the indenter is one of a cone indenter, a triangle indenter, and a square indenter.

17. The method as recited in claim 1, wherein the thin film comprises an upper sublayer and a lower sublayer; wherein the lower sublayer is on the substrate, and the upper sublayer is on the lower sublayer; wherein the at least one preformed notch is formed in the upper sublayer; and wherein the lower sublayer is harder than the substrate.

18. The method as recited in claim 17, where the upper sublayer is softer than the lower sublayer.

19. The method of claim 1 further comprising:
measuring a value of a load, P, on the indenter and a value of a displacement, h, of the indenter into the thin film and substrate, where the value of the load when the thin film fractures is $P_C$, and where the value of the displacement when the thin film fractures is $h_C$;
where the in-plane fracture toughness of the thin film is calculated based on $P_C$ and $h_C$.

20. The method as recited in claim 19, where the thin film is harder than the substrate.

21. The method as recited in claim 19, where P and h are continuously measured.

22. The method as recited in claim 21, where P is applied at a fixed rate.

23. The method as recited in claim 1, where the thin film has a top surface, and the notch is formed in the top surface.

24. The method of claim 1 further comprising:
measuring a cross-section of the notch after the indentation is formed;
wherein the in-plane fracture toughness is calculated based on the measured cross-section of the notch after the indentation is formed.

25. The method of claim 24, where the at least one notch has a crack tip;
where the in-plane fracture toughness of the thin film is calculated using the equation, $\kappa=\sqrt{mE\delta\sigma}$ where m is a dimensionless constant, E is the elastic modulus of the thin film, $\sigma$ is the yield strength of the thin film, and $\delta$ is the size of the crack tip opening for a stress on the thin film just before the crack tip extends into the thin film.

26. The method of claim 24, where the indenter is a Knoop indenter.

27. The method of claim 26, where the Knoop indenter has a diamond tip.

28. The method of claim 24, where the in-plane fracture toughness is calculated using finite element analysis.

29. An indentation apparatus comprising:
an indenter;
means for applying a load to the indenter;
means for monitoring a penetration depth of the indenter into a thin film on a substrate; and
means for calculating thin film fracture toughness of the thin film.

30. The indentation apparatus of claim 29, comprising:
means for detecting a sharp change in the penetration depth rate; and
means for detecting a critical value of the applied load at the time of the harp change in penetration depth rate of the indenter.

31. The indentation apparatus of claim 30, wherein the means for calculating thin film fracture toughness calculates the thin film fracture toughness of the thin film based on the detected critical value of the applied load.

32. A method of using an indentation apparatus, comprising:

placing an indenter in contact with a thin film on a substrate, where the thin film has a preformed notch thereon;

forcing the indenter into the thin film;

calculating a thin film in-plane fracture toughness of the thin film.

33. The method of using an indentation apparatus of claim 32 further comprising:

measuring a value of a load, P, on the indenter and a value of the displacement, h, of the indenter into the thin film and substrate, where the value of the load when the thin film fractures is $P_C$, and where the value of the displacement when the thin film fractures is $h_C$;

wherein the in-plane fracture toughness of the thin film is calculated based on $P_C$ and $h_C$.

34. The method of using an indentation apparatus of claim 32, wherein the thin film has at least one notch with a crack tip;

wherein the in-plane fracture toughness of the thin film is calculated using the equation, $\kappa = \sqrt{mE\delta\sigma}$, where m is a dimensionless constant, E is the elastic modulus of the thin film, $\sigma$ is the yield strength of the thin film, and $\delta$ is the value of the crack tip opening for a stress on the thin film just before the crack tip extends into the thin film.

* * * * *